US00PP21023P2

(12) United States Plant Patent
Saul

(10) Patent No.: US PP21,023 P2
(45) Date of Patent: May 25, 2010

(54) *ECHINACEA* PLANT NAMED 'ADAM SAUL'

(50) Latin Name: *Echinacea purpurea×Echinacea paradoxa*
Varietal Denomination: Adam Saul

(75) Inventor: Robert Saul, Atlanta, GA (US)

(73) Assignee: Itsaul Plants LLC, Atlanta, GA (US)

( * ) Notice: Subject to any disclaimer, the term of this patent is extended or adjusted under 35 U.S.C. 154(b) by 0 days.

(21) Appl. No.: 12/321,352

(22) Filed: Jan. 20, 2009

(51) Int. Cl.
*A01H 5/00* (2006.01)

(52) U.S. Cl. ..... Plt./428

(58) Field of Classification Search ..... Plt./428
See application file for complete search history.

*Primary Examiner*—Kent L Bell
(74) *Attorney, Agent, or Firm*—C. A. Whealy

(57) ABSTRACT

A new and distinct cultivar of *Echinacea* plant named 'Adam Saul', characterized by its upright and columnar plant habit; freely branching habit; numerous long-lasting single inflorescences with dark pink-colored ray florets with large inflorescence discs; strong flowering stems that hold the inflorescences upright; and good garden performance.

2 Drawing Sheets

Botanical designation: *Echinacea purpurea×Echinacea paradoxa.*

Cultivar denomination: 'ADAM SAUL'.

BACKGROUND OF THE INVENTION

The present invention relates to a new and distinct cultivar of *Echinacea* plant, botanically known as *Echinacea purpurea×Echinacea paradoxa*, and hereinafter referred to by the name 'Adam Saul'.

The new *Echinacea* plant originated from an open-pollination in August, 2004, of an unnamed selection of *Echinacea purpurea×Echinacea paradoxa*, not patented, as the female, or seed, parent with an unknown selection of *Echinacea purpurea×Echinacea paradoxa*, as the male, or pollen, parent. The new *Echinacea* plant was discovered and selected by the Inventor as a single flowering plant from within the progeny of the stated open-pollination grown in a controlled outdoor nursery environment in Chamblee, Ga. in February, 2005.

Asexual reproduction of the new *Echinacea* plant by tissue culture in a controlled environment in Chamblee, Ga. since May, 2005, has shown that the unique features of this new *Echinacea* plant are stable and reproduced true to type in successive generations.

SUMMARY OF THE INVENTION

Plants of the new *Echinacea* have not been observed under all possible environmental conditions. The phenotype may vary somewhat with variations in environment such as temperature and light intensity, without, however, any variance in genotype.

The following traits have been repeatedly observed and are determined to be the unique characteristics of 'Adam Saul'. These characteristics in combination distinguish 'Adam Saul' as a new and distinct cultivar of *Echinacea:*

1. Upright and columnar plant habit.
2. Freely branching habit.
3. Numerous long-lasting single inflorescences with dark pink-colored ray florets with large inflorescence discs.
4. Strong flowering stems that hold the inflorescences upright.
5. Good garden performance.

Compared to plants of the female parent selection, plants of the new *Echinacea* are more freely branching, more freely flowering and differ in ray floret coloration.

Plants of the new *Echinacea* can be compared to plants of *Echinacea purpurea* 'Magnus', not patented. In side-by-side comparisons conducted in Dahlonega, Ga., plants of the new *Echinacea* differed from plants of 'Magnus' in the following characteristics:

1. Plants of the new *Echinacea* had smaller leaves than plants of 'Magnus'.
2. Plants of the new *Echinacea* had smaller inflorescences than plants of 'Magnus'.
3. Plants of the new *Echinacea* were more freely flowering than of plants of 'Magnus'.
4. Inflorescences of plants of the new *Echinacea* were longer-lasting than inflorescences of plants of 'Magnus'.

BRIEF DESCRIPTION OF THE PHOTOGRAPHS

The accompanying photographs illustrate the overall appearance of the new *Echinacea*. The photographs show the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet comprises a side perspective view of a typical flowering plant of 'Adam Saul' grown in an outdoor nursery.

The photograph on the second sheet is a close-up view of typical inflorescences of 'Adam Saul'.

DETAILED BOTANICAL DESCRIPTION

The aforementioned photographs and following observations and measurements describe plants grown in Dahlonega, Ga. during the spring and summer in an outdoor nursery and under conditions and practices which approximate those generally used in commercial *Echinacea* production. During the production of the plants, day temperatures ranged from about −2° C. to about 33° C. and night temperatures ranged from about −17° C. to about 21° C. Measurements and numerical values represent averages for typical flowering plants. Plants had been growing for two years when the photographs and description were taken. In the following description, color references are made to The Royal Horticultural Society Colour Chart, 2001 Edition, except where general terms of ordinary dictionary significance are used.

Botanical classification: *Echinacea purpurea*×*Echinacea paradoxa* 'Adam Saul'.

Parentage:

*Female parent*.—Unnamed selection of *Echinacea purpurea*×*Echinacea paradoxa*, not patented.

*Male parent*.—Unknown selection of *Echinacea purpurea*×*Echinacea paradoxa*, not patented.

Propagation:

*Type*.—By tissue culture.

*Time to initiate roots*.—About two weeks at 22° C.

*Time to produce a rooted young plant, summer*.—About four to five weeks at 32° C.

*Time to produce a rooted young plant, winter*.—About six weeks at 26° C. to 29° C.

*Root description*.—Fleshy, medium in thickness; white in color.

*Rooting habit*.—Freely branching; moderately dense.

Plant description:

*Plant form/growth habit*.—Upright and columnar plant habit; freely basal branching with about nine to eleven basal branches; terminal and axillary inflorescences potentially developing at every node and are held upright on strong peduncles; moderately vigorous growth habit.

*Plant height*.—About 35 cm.

*Plant diameter or spread*.—About 33 cm. Basal branches: Length: About 30 cm. Diameter: About 4.5 mm. Internode length: About 4.5 cm. Aspect: Upright. Strength: Strong. Texture: Pubescent; rough. Color: Close to 144A and 144B; occasionally overlain with close to 59A.

Foliage description:

*Arrangement*.—Alternate, simple.

*Length*.—About 9.5 cm.

*Width*.—About 2.75 cm.

*Shape*.—Narrowly ovate to lanceolate.

*Apex*.—Acute.

*Base*.—Attenuate.

*Margin*.—Entire.

*Texture, upper and lower surfaces*.—Pubescent; rough.

*Venation pattern*.—Pinnate.

*Color*.—Developing and fully expanded leaves, upper surface: Close to 147A; venation, close to 147B. Developing and fully expanded leaves, lower surface: Close to 147B; lateral veins, close to 147B; midvein, close to 150D.

*Petiole*.—Length: About 4.6 cm. Diameter: About 3 mm. Texture, upper and lower surfaces: Smooth, glabrous. Color, upper and lower surfaces: Close to 150D.

Inflorescence description:

*Appearance*.—Rotate single inflorescence form with ray and disc florets; inflorescences terminal or axillary; inflorescences potentially developing at every node with about 33 open inflorescences per plant at one time; inflorescences held upright on strong peduncles.

*Fragrance*.—Moderate; sweet.

*Time to flower*.—Plants flower continuously from the spring through the summer in Georgia.

*Inflorescence longevity*.—Inflorescences maintain good substance for about four weeks on the plant; inflorescences persistent.

*Inflorescence bud*.—Height: About 7.5 mm. Diameter: About 9 mm. Shape: Oblate. Color: Close to 147B.

*Inflorescence size*.—Diameter: About 6.2 cm. Depth (height): About 2.3 cm. Disc diameter: About 2.5 cm. Receptacle height: About 8 mm. Receptacle diameter: About 6 mm. Receptacle shape: Conical. Receptacle color: Close to 155D.

*Ray florets*.—Length: About 3 cm. Width: About 9 mm. Shape: Elongated oblong. Apex: Emarginate. Base: Attenuate; fused into a short corolla tube. Texture, upper and lower surfaces: Smooth, glabrous; satiny. Number of ray florets per inflorescence: About 16 arranged in a single whorl. Aspect: Initially upright to eventually reflexing; mostly flat. Color: When opening, upper surface: Close to 73A. When opening, lower surface: Close to 73C. Fully opened, upper surface: Close to 73A to 73B; color becoming closer to 73C with development. Fully opened, lower surface: Close to 73C to 73D; color becoming closer to 155D with development.

*Disc florets*.—Shape: Tubular; apex five-pointed. Length: About 8 mm. Diameter: About 2 mm. Number of disc florets per inflorescence: About 237. Texture: Smooth, glabrous. Color: Immature: Apex: Close to 59A. Mid-section and base: Close to 155D. Mature: Apex: Close to 59A. Mid-section: Close to 144A. Base: Close to 155D.

*Receptacle spines*.—Quantity: One per disc floret. Length: About 1.5 cm. Width: About 1 mm. Shape: Lanceolate to acicular. Apex: Sharply acute. Base: Tapering. Texture: Smooth, glabrous. Color: Apex: Close to 23A. Mid-section: Close to 144A. Base: Close to 155D.

*Phyllaries*.—Quantity per inflorescence: About 45 in about three whorls. Length: About 9 mm. Width: About 2.5 mm. Shape: Lanceolate. Apex: Acute. Base: Truncate. Margin: Entire. Texture, upper and lower surfaces: Pubescent. Color, upper and lower surfaces: Close to 147B.

*Peduncles*.—Length, terminal peduncle: About 7 cm. Length, uppermost axillary peduncle: About 11 cm. Diameter: About 3 mm. Angle, terminal peduncles: Erect. Angle, axillary peduncles: About 40° from vertical. Strength: Strong. Texture: Pubescent; rough. Color: Close to 144A to 144B; occasionally overlain with close to 59A.

*Reproductive organs*.—Androecium: Stamens per disc floret: One. Filament length: About 7 mm. Filament color: Close to 145D. Anther shape: Oblong. Anther length: Less than 1 mm. Anther color: Close to 146C to 146D. Pollen amount: None observed. Gynoecium: Pistil length: About 7 mm. Stigma shape: Cleft; reflexed. Stigma color: Close to 59A. Style length: About 5.5 mm. Style color: Close to 59A. Ovary color: Close to 157A. Seeds/fruits: Seed and fruit development have not been observed on plants of the new *Echinacea*.

Disease/pest resistance: Plants of the new *Echinacea* have not been shown to be resistant to pathogens and pests common to *Echinacea*.

Garden performance: Plants of the new *Echinacea* have been observed to have good garden performance and to tolerate rain, wind and temperatures ranging from about −17° C. to about 37° C.

It is claimed:

1. A new and distinct *Echinacea* plant named 'Adam Saul' as illustrated and described.

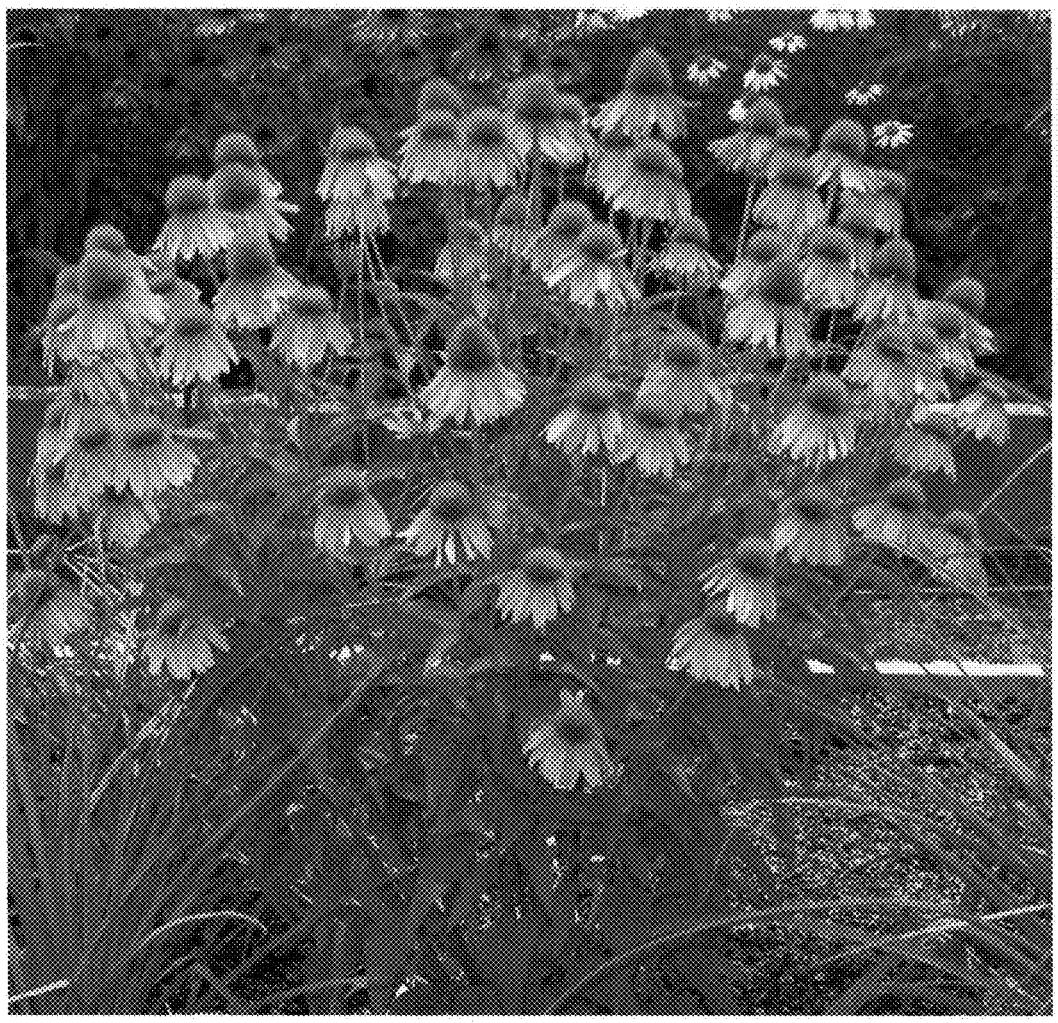

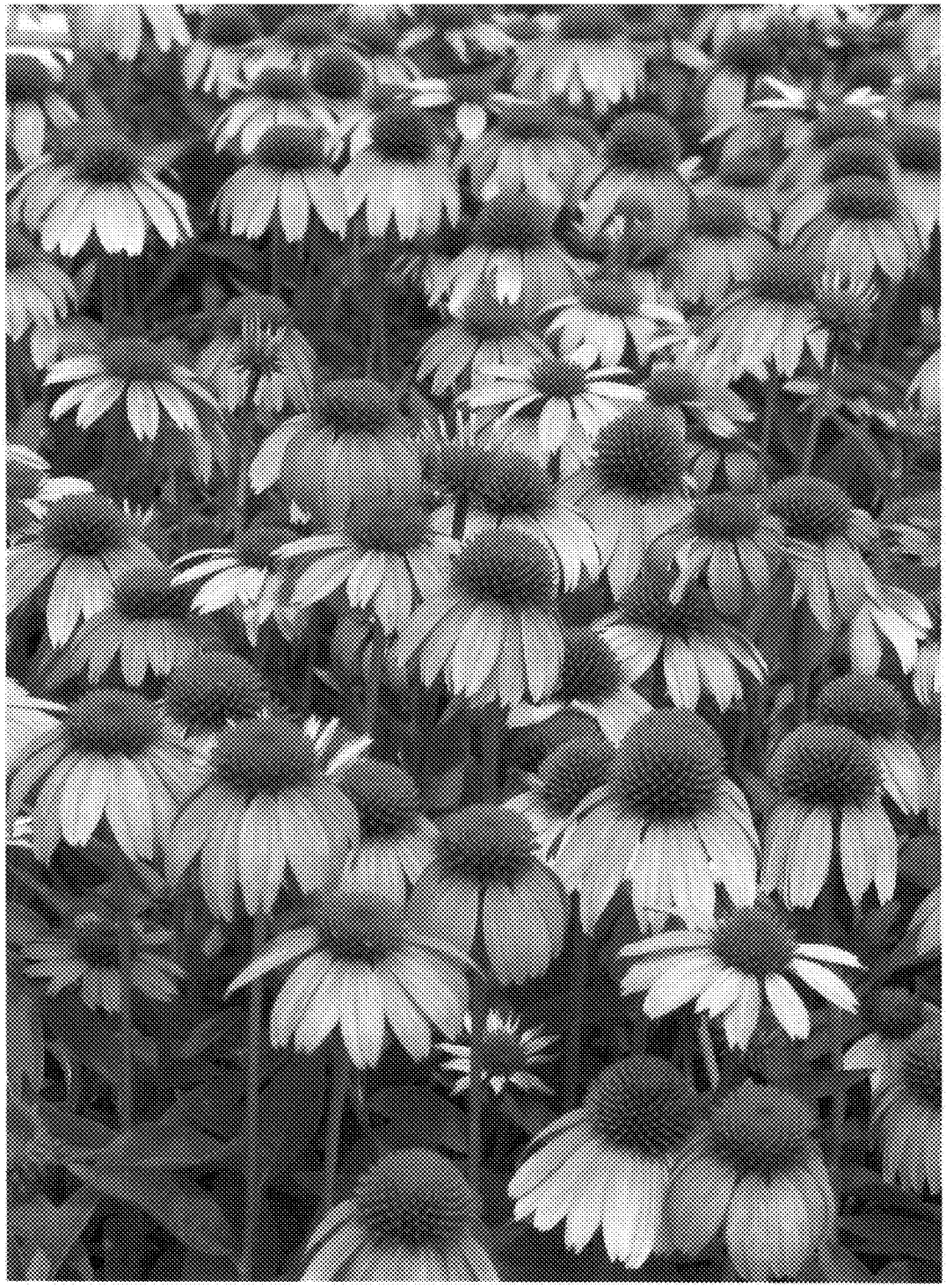

* * * * *